(12) United States Patent
Boehm et al.

(10) Patent No.: US 9,596,876 B2
(45) Date of Patent: Mar. 21, 2017

(54) METHOD FOR STIMULATING THE INTESTINAL FLORA

(71) Applicant: N.V. Nutricia, Zoetermeer (NL)

(72) Inventors: Günther Boehm, Leipzig (DE); Bernd Stahl, Utrecht (NL); Jan Knol, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 14/973,166

(22) Filed: Dec. 17, 2015

(65) Prior Publication Data

US 2016/0100618 A1 Apr. 14, 2016

Related U.S. Application Data

(63) Continuation of application No. 12/083,612, filed as application No. PCT/EP2006/010159 on Oct. 20, 2006, now abandoned.

(30) Foreign Application Priority Data

Oct. 21, 2005 (EP) ..................... 05023029

(51) Int. Cl.

| | | |
|---|---|---|
| A23L 1/30 | (2006.01) | |
| A61K 31/7016 | (2006.01) | |
| A23C 9/123 | (2006.01) | |
| A23C 9/20 | (2006.01) | |
| A61K 31/202 | (2006.01) | |
| A61K 31/702 | (2006.01) | |
| A61K 31/7068 | (2006.01) | |
| A61K 31/7072 | (2006.01) | |
| A61K 31/7076 | (2006.01) | |
| A61K 31/708 | (2006.01) | |
| A61K 31/732 | (2006.01) | |
| A61K 31/734 | (2006.01) | |
| A61K 35/745 | (2015.01) | |
| A61K 35/747 | (2015.01) | |
| A61K 35/74 | (2015.01) | |
| A61K 47/36 | (2006.01) | |
| A61K 31/7064 | (2006.01) | |

(52) U.S. Cl.
CPC .......... *A23L 1/3014* (2013.01); *A23C 9/1234* (2013.01); *A23C 9/203* (2013.01); *A23C 9/206* (2013.01); *A23L 29/065* (2016.08); *A23L 33/10* (2016.08); *A23L 33/12* (2016.08); *A23L 33/135* (2016.08); *A23L 33/17* (2016.08); *A23L 33/21* (2016.08); *A23L 33/40* (2016.08); *A61K 31/202* (2013.01); *A61K 31/702* (2013.01); *A61K 31/708* (2013.01); *A61K 31/7016* (2013.01); *A61K 31/7064* (2013.01); *A61K 31/7068* (2013.01); *A61K 31/7072* (2013.01); *A61K 31/7076* (2013.01); *A61K 31/732* (2013.01); *A61K 31/734* (2013.01); *A61K 35/74* (2013.01); *A61K 35/745* (2013.01); *A61K 35/747* (2013.01); *A61K 47/36* (2013.01); *A23V 2002/00* (2013.01); *A23Y 2220/85* (2013.01); *A23Y 2300/19* (2013.01); *A23Y 2300/21* (2013.01); *A23Y 2300/25* (2013.01); *A23Y 2300/29* (2013.01); *A23Y 2300/31* (2013.01); *A23Y 2300/41* (2013.01); *A23Y 2300/45* (2013.01); *A23Y 2300/49* (2013.01); *A23Y 2300/55* (2013.01); *A23Y 2300/59* (2013.01); *A23Y 2300/65* (2013.01)

(58) Field of Classification Search
CPC .......... C12R 1/07; A23Y 2300/29; C12N 1/20
See application file for complete search history.

(56) References Cited

U.S. PATENT DOCUMENTS

| | | | |
|---|---|---|---|
| 4,994,442 | A | 2/1991 | Gil et al. |
| 5,472,952 | A | 12/1995 | Smidt et al. |
| 5,895,648 | A | 4/1999 | Cavaliere Vesely et al. |
| 6,511,696 | B2 | 1/2003 | Gohman et al. |
| 6,613,549 | B2 | 9/2003 | Reid et al. |
| 7,410,653 | B1 | 8/2008 | Blareau et al. |
| 8,227,448 | B2 | 7/2012 | Van Laere et al. |
| 8,715,769 | B2 | 5/2014 | Schmitt et al. |
| 9,107,438 | B2 | 8/2015 | Schmitt et al. |

(Continued)

FOREIGN PATENT DOCUMENTS

| | | |
|---|---|---|
| EP | 0 847 244 B1 | 3/2001 |
| EP | 1 105 002 B1 | 6/2001 |

(Continued)

OTHER PUBLICATIONS

Artikel zum Thema, aid-infodienst-Ernahrung-Richtig Essen-nahrstoffempfehlungen, http://www.aid.de/eraehrung/naehrstoffempfehlungen_hauptnaehrstoffe.php (2010) pp. 1-5. (French Language).
"Report of the Scientific Committee on Food on the Revision of Essential Requirements of Infant Formulae and follow-on Formulae," (2003) (See p. 63, 4th paragraph).
Bakker-Zierikzee et al., "Effects of Infant Formula Containing a Mixture of Galacto- and Fructooligosaccharides or Viable Bifidobacterium Animalis on the Intestinal Microflora During the First 4 Months of Life," British Journal of Nutrition, 94:783-790 (2005).

(Continued)

*Primary Examiner* — Ruth Davis
(74) *Attorney, Agent, or Firm* — Foley & Lardner LLP; Sunit Talapatra

(57) ABSTRACT

The present invention relates to methods for feeding and to compositions to be administered to infants delivered via caesarian section and in particular to the use of a) at least two different microorganisms; or b) at least one microorganism and at least one indigestible oligosaccharide; or c) at least two different *Bifidobacteria* species, subspecies or strains for the manufacture of a composition for enteral administration to an infant delivered via caesarean section. Thereby it is possible to stimulate the healthy development of the intestinal flora of said infants.

7 Claims, No Drawings

(56) References Cited

U.S. PATENT DOCUMENTS

| | | |
|---|---|---|
| 2003/0022863 A1 | 1/2003 | Stahl et al. |
| 2004/0062758 A1 | 4/2004 | Mayra-Makinen et al. |
| 2004/0071824 A1 | 4/2004 | Van Laere et al. |
| 2004/0072791 A1 | 4/2004 | Kunz et al. |
| 2004/0072794 A1 | 4/2004 | Kaup et al. |
| 2004/0143013 A1 | 7/2004 | Schade et al. |
| 2006/0018890 A1 | 1/2006 | Isolauri et al. |
| 2006/0233773 A1 | 10/2006 | Herz et al. |
| 2007/0031537 A1 | 2/2007 | Secretin |
| 2007/0248649 A1 | 10/2007 | Sawatzki et al. |
| 2007/0274983 A1 | 11/2007 | Kluijtmans et al. |
| 2008/0199446 A1 | 8/2008 | Vriesema et al. |
| 2009/0162323 A1 | 6/2009 | Boehm et al. |
| 2011/0150851 A1 | 6/2011 | Schmitt et al. |
| 2016/0100618 A1 | 4/2016 | Boehm et al. |

FOREIGN PATENT DOCUMENTS

| | | |
|---|---|---|
| EP | 1 364 586 A1 | 11/2003 |
| EP | 1 481 682 A1 | 12/2004 |
| EP | 1 634 599 A1 | 3/2006 |
| WO | WO-98/06418 A1 | 2/1998 |
| WO | WO-00/08948 A | 2/2000 |
| WO | WO-00/08984 | 2/2000 |
| WO | WO-0101785 | 1/2001 |
| WO | WO-01/78530 A2 | 10/2001 |
| WO | WO-03/043445 A1 | 5/2003 |
| WO | WO-2004/032639 A1 | 4/2004 |
| WO | WO-2004/032651 A1 | 4/2004 |
| WO | WO-2004/067013 A1 | 8/2004 |
| WO | WO-2004/069156 A2 | 8/2004 |
| WO | WO-2004/093899 A1 | 11/2004 |
| WO | WO-2004/112507 A1 | 12/2004 |
| WO | WO-2004/112509 A2 | 12/2004 |
| WO | WO-2005/039318 A1 | 5/2005 |
| WO | WO 2005/039319 * | 5/2005 |
| WO | WO-2005/039319 A1 | 5/2005 |
| WO | WO-2005/039597 A2 | 5/2005 |
| WO | WO-2005/051088 A2 | 6/2005 |
| WO | WO-2005/110121 A1 | 11/2005 |
| WO | WO-2005/122790 A1 | 12/2005 |
| WO | WO-2006/087391 A1 | 8/2006 |
| WO | WO-2006/108824 A1 | 10/2006 |
| WO | WO-2006/115412 A2 | 11/2006 |
| WO | WO-2007/045502 A1 | 4/2007 |
| WO | WO-2007/046698 A1 | 4/2007 |

OTHER PUBLICATIONS

Bennet et al., "Development of the Faecal Anaerobic Microflora After Caesarean Section and Treatment with Antibiotics in Newborn Infants," Infection, 15(5):332-336 (1987).

Bennet et al., "Transient Colonization of the Gut of Newborn Infants by Orally Administered Bifidobacteria and Lactobacilli," Acta Paediatrica, 81(10):784-787 (1992).

Bennet et al., "Fecal Bacterial Microflora of Newborn Infants During Intensive Care Management and Treatment With Five antibiotic Regimens," The Pediatric Infectious Disease Journal, 5(5):533-539 (1986) http://www.ncbi.nlm.nih.gov/pubmed/376418.

Bezirtzoglou E., "The intestinal Microflora During the First Weeks of Life," Anaerobe, 3:173-177 (1997).

Bezirtzoglou et al., "Apparition of Clostridium Sp. and Bacteroides in the Intestine of the Newborn Delivered by Cesarian Section," Comparative Immunology, Microbiology and Infectious Diseases, 13(4):217-221 (1990).

Bezirtzoglou et al., "Effect of the Feeding Practices on the Establishment of Bacterial Interactions in the Intestine of the Newborn Delivered by Cesarian Section," Journal of Perinatal Medicine, 17:139-143 (1989), Department of Microbiology, University of Ioannina, Ioannina, Greece, and Faculty of Pharmacy, Microbiology, University of Lille, Lille, France.

Bin-Nun et al., "Oral Probiotics Prevent Necreotizing Enterocolitis in Very Low Birth Weight Neonates," Journal of Pediatrics, 147(2):192-196 (2005).

Boehm et al., "Supplementation of a bovine milk formula with an oligosaccharide mixture increases counts of faecal bifidobacteria in preterm infants," Arch. Dis. Child Fetal Neonatal Ed., (2002), B6, pp. F178-F181.

Braunwald et al. (Editors), "Harrison's Principles of Internal Medicine," Eleventh Edition, McGraw-Hill Book Company, 502-503 (1987).

Bruzzese et al., "Early Administration of GOS/FOS Prevents Intestinal and Respiratory Infections in Infants," Journal of Pediatric Gastroenterology and Nutrition, 42(5):E95 (2006).

Calder et al., "Early Nutrition and Immunity—Progress and Perspectives," British Journal of Nutrition, 96:774-790 (2006).

Carver, D.J., "Advances in Nutritional Modifications of Infant Formulas," The American Journal of Clinical Nutrition, 77:1550S-1554S (2003).

Cibik et al., "Bacterial Intestinal Flora: Development, Characteristics and Influences of the Type of Feeding," Archives de Pediatrie, 11:573-575 (2004) (French Language).

Collins, et al., "Probiotics, Prebiotics, and Synbiotics: Approaches for Modulating the Microbial Ecology of the Gut," the American Journal of Clinical Nutrition, 69:1052S-1057S (1999).

Commission, "Modifiant la Directive 91/321/CEE Concernant Les Préparations Pour Nourrissons et Les Préparations de Suite," Directive 96/4/CE de la Commission, Journal officiel des Communautés européennes, 49:12-16 (1996) (French Language).

Commission, "Concernant les Préparations Pour Nourissons et les Préparations de Suite, Directive de la Commission," Journal officiel des Communautés européennes, 175:35-48 (1991) (French Language).

Cosgrove, "Nucleotides," Nutrition, Perinatal and Infant Nutrition, 14(10):748-751 (1998).

Debley et al. "Childhood Asthma Hospitalization Risk After Cesarean Delivery in Former Term and Premature Infants," Annals of Allergy Asthma Immunology, 94:228-233 (2005).

Dunstan et al., "Maternal Fish Oil Supplementation in Pregnancy Reduces Interleukin-13 Levels in Cord Blood of Infants at High risk of Atopy," Clinical & Experimental Allergy, 33:442-448 (2003).

Eggesbo et al., "Is Delivery by Cesarean Section a Risk Factor for Food Allergy?" Journal of Allergy Clinical Immunology, 112(2):420-426 (2003).

Fanaro et al., "Acidic Oligosaccharides from Pectin Hydrolysate as New Component for Infant Formulae: Effect on Intestinal Flora, Stool Characteristics, and pH," Journal of Pediatric Gastroenterology and Nutrition, 41:186-190 (2005).

Fanaro et al., "Intestinal Microflora in Early Infancy: Composition and Development," Acta Paediatrica, Universitetsforlaget, Oslo, Norway, 441:48-55 (2003).

Fanaro et al., "Galacto-Oligosaccharides and Long-Chain Fructo-Oligosaccharides as Prebiotics in Infant Formulas: A Review," Acta Paediatrica Supplement, 94(449):22-26 (2005).

Favier et al., Molecular Monitoring of Succession of Bacterial communities in Human Neonates, Applied and Environmental Microbiology, 68(1):219-226 (2002).

Field et al., "Polyunsaturated Fatty Acids and T-Cell Function: Implications for the Neonate," Lipids, 36(9):1025-1032 (2001).

Fructooligosaccharide, From Wikipedia, http://en.wikipedia.org/wiki/Fructooligosaccharide, pp. 1-4, Jun. 13, 2011.

Fuller, "Probiotics in Human Medicine," GUT, An International Journal of Gastroenterology and Hepatology, 32(4):439-442 (1991).

Gewolb et al., "Stool Microflora in Extremely Low Birthweight Infants," Archives of Disease in Childhood Fetal and Neonatal Edition, 80:F167-F173 (1999).

Gibson et al., "Dietary Modulation of the Human Colonic Microbiota: Introducing the Concept of Prebiotics," Journal of Nutrition, Critical Review, 125(6):1401-1412 (1995).

Goedhart et al., "The Composition of Human Milk as a Model for the Design of Infant Formulas: Recent Findings and Possible Applications," Nutrition Research Reviews, 7:1-23 (1994).

Grönlund, Minna-Maija, et al., "Fecal Microflora in Healthy Infants Born by Different Methods of Delivery: Permanent Changes in Intestinal Flora After Cesarean Delivery," Journal of Pediatric Gastroenterology and Nutrition, 28(1):19-25 (1999).

(56) References Cited

OTHER PUBLICATIONS

Hakansson et al., "Caesarean Section Increases the Risk of Hospital Care in Childhood for Asthma and Gastroenteritis," Clinical & Experimental Allergy, 33:757-764 (2003).
Hall et al., "Factors Influencing the Presence of Faecal Lactobacilli in Early Infancy," Archives of Desease in Childhood, 65(2):185-188 (1990).
Hallstrom et al., "Effects of the Mode of Delivery and Necrotising Enterocolitis on the Intestinal Microflora in Preterm Infants," European Journal of Clinical Microbiology and Infectious Diseases, 23:463-470 (2004).
Heinrich, Negele, et al., "Mode of Delivery and Development of Atopic Disease During the First 2 Years of Life," Pediatric Allergy and Immunology, 15(1):48-54 (2004).
Heyman et al., "Effects of Specific Lactic Acid Bacteria on the Intestinal Permeability to Macromolecules and the Inflammatory Condition," Acta Paediatrica, Universitetsforlaget, Oslo, 94(449):34-36 (2005).
Janas et al, "The Nucleotide Profile of Human Milk," Pediatric Research, 16(8):659-662 (1982).
Kirjavainen et al., "Probiotic Bacteria in the Management of Atopic Disease: Underscoring the Importance of Viability," Journal of Pediatric Gastoenterology and Nutrition, 36:223-227 (2003).
Knol et al., "Colon Microflora in Infants Fed Formula with Galacto- and Fructo-Oligosaccharides: More Like Breast-Fed Infants," Journal of Pediatric Gastroenterology and Nutrition, 40:36-42 (2005).
Koletzko et al., "Polyunsaturated Fatty Acids in Human Milk and Their Role in Early Infant Development," Journal of Mammary Gland Biology and Neoplasia, Plenum Press, New York, NY, 4(3):269-284 (1999).
Kunz et al., "Oligosaccharides in Human Milk: Structural, Functional, and Metabolic Aspects," Annual Review of Nutrition, 20:699-722 (2000).
Laubereau et al., "Caesarean Section and Gastrointestinal Symptoms, Atopic Dermatitis, and Sensitization During the First Year of Life," Archives if Disease in Childhood, 89:993-997 (2004).
"La selection Udo Probiotiques: melange pour nourrissons," http://www.florahealth.com/flora/home/canadafr/products/TG8.htm#1966.
Life Start® —Dairy (1.25 oz. powder), Natren, The Probiotic Specialist Recognized Worldwide, 2 pgs., (2006).
Lin et al. "Oral Probiotics Reduce the Incidence and Severity of necrotizing Enterocolitis in Very Low Birth Weight Infants," Pediatrics Official Journal of the American Academy of Pediatrics, 2005, vol. 115, No. 1, pp. 1-4.
Marini et al., "Pro- and pre-biotics administration in preterm infants: colonization and influence on faecal flora," Acta Paediatrica Scandinavica Supplement, 91(441):80-81 (2003) (Abstract Only).
Martin et al., "Isolation of Bifidobacteria From Breast Milk and Assessment of the Bifidobacterial population by PCR-Denaturing Gradient Gel Electrophoresis and Quantitative Real-Time PCR," Applied and Environmental Microbiology, 75(4):965-969 (2009).
Martin et al., "The Commensal Microflora of Human Milk: New Perspectives for Food Bacteriotherapy and Probiotics," Trends in Food Science & Technology, 15(3-4):121-127 (2004).
Martin-Sosa et al., "Sialyloligosaccharides in Human and Bovine Milk and in Infant Formulas: Variations with the Progression of Lactation," Journal of Dairy Science, 86:52-59 (2003).
McVay et al., "Formula Fortified With Live Probiotic Culture Reduces Pulmonary and Gastrointestinal Bacterial Colonization and Translocation in a Newborn Animal Model," Journal of Pediatric Surgery, 43:25-29 (2008).
McVeagh et al., "Human Milk Oligosaccharides: Only the Breast," Journal of Pediatric Child Health, 33(4):281-286 (1997).
Millar et al., "Probiotics for preterm infants," www.archdischild.com, Archives of Disease in Childhood: Fetal & Neonatal, 88(5):F354-F358 (2003).

Morishita et al., Galactooligosaccharide in Combination With Bifidobacterium and Bacteroides Affects the Population of Clostridium Perfringens in the Intestine of Gnotobiotic Mice, Nutrition Research, 22:1333-1341 (2002).
Moro et al., "A Mixture of Prebiotic Oligosaccharides Reduces the Incidence of Atopic Dermatitis During the First Six Months of Age," Archives of Disease in Childhood: Fetal & Neonatal, 91:814-819 (2006).
Moro et al., "Dosage-Related Bifidogenic Effects of Galacto- and Fructooligosaccharides in Formula-Fed Term Infants," Journal of Pediatric Gastroenterology and Nutrition, 34(3):291-295 (2002).
Mullane N.R. et al., "Enterobacter Sakazakii: Biological Properties and Significance in Dried Infant Milk formula (IMF) Powder," International Journal of Dairy Technology, 59(2):102-111 (2006).
Nadkarni et al., Determination of Bacterial Load by Real-Time PCR Using a Broad-Range (Universal) Probe and Primers Set, Microbiology, 148:257-266 (2002).
Neut et al., "Bacterial Colonization of the Large Intestine in Newborns Delivered by Cesarean Section," Zbl Bakt Hyg A, 266:330-337 (1987).
Nutritional Quality of Milkfat reference (accessible at: www.idfdairynutrition.org/Files/media/FactSheetsHP/Final-HP-Factsheet-Milkfat-080125.pdf) (published 2008; last accessed May 5, 2014).
Ouwehand et al., "The Mucus Binding of Bifidobacterium Lactis Bb 12 is Enhanced in the Presence of Lactobacillus GG and Lact. Delbrueckil Subsp. Bugaricus," Applied Microbiology, 30(1):10-13 (2000), Department of Biochemistry and Food Chemistry, University of Turku, Finland.
Rivero, M., "Effect of a New Infant Formulae Enriched Prebiotics, Probiotics, Nucleotides and Lc-Pufa's on Infants Recovery After an Infection," Journal of Pediatric Gastroenterology and Nutrition, 39(1):S482-S483, Jun. 2004.
Satokari et al., "Bifidobacterial Diversity in Human Feces Detected by Genus-Specific PCR and Denaturing Gradient Gel Electrophoresis," Applied and Environmental Microbiology, 67(2):504-513 (2001).
Satorkari et al., "Molecular Approaches for the Detection and Identificationof Bifidobacteria and Lactobacilli in the Human Gastrointestinal Tract," System Applied Mocrobiology, 26:572-584 (2003).
Scherz et al., "Food Compositions and Nutrition Tables," Medpharm Scientific Publishers Suttgart, 6-7 (1994).
Thillay et al., "Ave Cesar, les bebes qui seront allergiques to detestent!," Arch. Dis. Child, Allergie, France, 89(11):993-997 (2004) (French Language).
Vandenplas, "Oligosaccharides in Infant Formula," British Journal of Nutrition (2002) vol. 87, Suppl. 2, pp. S293-S296.
Varel et al., "Nutritional Features of Baceroides Fragilis Subsp. Fragilis," Applied Microbiology, 18(2):251-257 (1974).
Vidal Dictionary 2001, 32-33 (partial) (see description of Infant Formula Conformil) (French Language).
Vidal Dictionary 2005, 98-99, 111, 112, 121 (see description of Infant Formulas Enfamil Premium on p. 112 and Gallia Calisma on p. 121). (French Language).
Wikipedia, "Galacto-oligosaccharides", Jun. 28, 2013; http://www.en.wikipedia.org/wiki/galactooligosaccharide, p. 1.
Wikipedia, "Raffinose", Jun. 28, 2013, http://en.wikipedia.org/wiki/raffinose, p. 1.
Willemsen et al., "Specific Poly-Unsaturated Fatty Acids Support Intestinal Barrier Integrity and Reduce Il-4 Mediated Barrier Disruption: PG4-01," Journal of Pediatric Gastroenterology and Nutrition, 40(5):654 (2005).
Xaus et al., "Infant Nutrition as Target," Nutrafoods, 3(2):13-21 (2004).

\* cited by examiner

METHOD FOR STIMULATING THE INTESTINAL FLORA

CROSS-REFERENCE TO RELATED APPLICATIONS

This application is a Continuation of U.S. patent application Ser. No. 12/083,612, filed Apr. 15, 2008, which is the National Phase Application of International Patent Application No. PCT/EP2006/010159, filed Oct. 20, 2006, published on Apr. 26, 2007 as WO 2007/045502 A1, which claims priority to European Patent Application No. 05023029.1, filed Oct. 21, 2005. The contents of these applications are herein incorporated by reference in their entirety.

FIELD OF THE INVENTION

The present invention relates to methods for feeding and to compositions to be administered to infants delivered via caesarian section.

BACKGROUND OF THE INVENTION

When formulating nutrition for infants, breast milk is used as the gold standard. Ingredients in particular of non-human origin are normally combined to mimic the compositional features and physiological effects of the human breast milk.

One important aspect of human milk is that it provides energy and fluids to the infant. Besides providing energy, human breast milk contains many additional components, which aim to maintain the health of the infant. Human breast milk for example contains prebiotic fiber, which stimulates the development of a healthy intestinal flora. A healthy intestinal flora has numerous positive effects on the infant, such as a reduced incidence of infections and a strengthened immune system.

Several commercially available infant milk formulae contain ingredients that aim to stimulate the development of the intestinal flora. Infant formulae can for example contain prebiotic fibers or live probiotic organisms. The prebiotic fibers normally pass undigested through the upper gastrointestinal tract and selectively stimulate the growth of beneficial bacteria in the colon. Live probiotic bacteria increase specific bacterial counts in the intestine.

EP 1105002 describes a prebiotic carbohydrate mixture comprising one or more soluble oligosaccharides and one or more soluble polysaccharides, with at least 80 wt. % of each being prebiotic.

WO 2005039319 describes a preparation comprising *Bifidobacterium breve* and a mixture of non-digestible carbohydrates for non- or partially breast-fed infants as well as the use thereof for the treatment or prevention of immune disorder in non- or partially breast-fed infants.

SUMMARY OF THE INVENTION

Infant formulae are normally designed to mimic the development of an intestinal flora in an infant receiving human breast milk, with the implication that all infants react similar to human breast milk and infant formula. However, the present inventors have found that a sub-population of infants, namely those infants delivered via caesarian section, will react differently because their intestinal flora at birth is completely different from the intestinal flora of infants born via the vaginal route. In particularly, the profile and content of *Bifidobacteria* species of infants delivered via caesarean section is different from the intestinal profile and content of *Bifidobacteria* species of infants delivered via the vaginal route.

The present inventors have analyzed the intestinal flora of newborns after caesarean delivery and newborns after vaginal delivery. It was surprisingly found that great differences exist between the two groups in composition of the intestinal flora. Particularly infants born via the vaginal route contain at least about three different *Bifidobacteria* species, whereas the infants born via cesarean section lack the most important *Bifidobacteria* species.

It was also found that the infants born via caesarian section particularly lack *Bifidobacteria breve*, *Bifidobacterium infantis*, *Bifidobacterium bifidum*, *Bifidobacterium catenulatum*, *Bifidobacterium adolescentis* and *Bifidobacterium longum*. These species were present in the flora of most infants born via the vaginal route.

Because the intestinal flora plays a crucial role in the development of the infant, in particular the stimulation of the immune system and resistance against infections, it is of utmost importance to stimulate the healthy development of the intestinal flora of infants born via cesarean section.

Furthermore the newborns delivered via caesarian section lacked a biodiversity in their intestinal flora. Only one or two different species of *Bifidobacteria* were detected in infants born via c-section, while the intestinal flora of newborns delivered via the vaginal route normally contains several different species of *Bifidobacteria*. The present inventors believe that these observations are indicative for a general lack of a species variety in the intestinal tract of infants delivered via c-section. The biodiversity is of great importance for the achieving the desired physiological effects and optimally stimulate the health of the infant.

Natren® produces the probiotic product Life Start® which is designed specifically for infants and suitable for infants delivered via caesarean section. Life Start® is made with *Bifidobacterium infantis*. Because the Life Start® product contains only one single *Bifidobacteria* species, the benefits for the infant will be very limited.

Particularly unexpected is also the observation that improvements of infant health can be achieved even when infants are fed with breast milk. In the case where infants are delivered via cesarean section, breast milk is (in most cases) the best nutrition for the infant. However, the breast milk also does not instantaneously result in a similar flora as obtained in infant born via vaginal delivery. The present method is therefore also advantageously used when infant receive human breast milk.

Hence, the present invention particularly aims to: a) increase the occurrence of particular species in the intestinal flora of infants born via caesarian section; b) increase the biodiversity of microorganisms in the intestinal flora; and/or c) stimulate the growth of beneficial microorganisms, particularly *Bifidobacteria*.

Hence in one aspect the present invention provides a method for stimulating the healthy development of the intestinal flora of infants born via caesarian section by administrating a composition containing:
- at least two different microorganisms;
- at least one microorganism and at least one indigestible oligosaccharide; or
- at least two different *Bifidobacteria* species, subspecies or strains.

The microorganism will increase the biodiversity of the infants flora, while the indigestible oligosaccharides stimulate the development and growth of inherent and administered microorganisms.

The composition to be administered in the present method preferably contains multiple different bacterial species, preferably multiple *Bifidobacteria* species. This results in the optimal stimulation of the intestinal flora of the caesarean delivered infants.

DETAILED DESCRIPTION OF THE PREFERRED EMBODIMENTS

The present invention provides a method for feeding infants, said method comprising enterally administering a composition to an infant delivered via caesarean section, said composition comprising: a) at least two different microorganisms; or b) at least one microorganism and at least one indigestible oligosaccharide; or c) at least two different *Bifidobacteria* species, subspecies or strains.

In a further aspect the present invention provides a method for stimulating the health of an infant delivered via caesarean section, comprising administering to the infant and within 100 hours after birth a composition containing microorganisms and/or indigestible oligosaccharides.

In still a further aspect the present invention provides a method for the manufacture of infant nutrition suitable for infant born via cesarean section comprising admixing: A) human breast milk; and B) a composition comprising: i) at least two different microorganisms; or ii) at least one microorganism and at least one indigestible oligosaccharide; or iii) at least two different *Bifidobacteria* species, subspecies or strains.

In still a further aspect, the present invention provides a composition comprising at least four *Bifidobacteria* species, subspecies or and/or strains selected from the group consisting of *Bifidobacterium breve, Bifidobacterium infantis, Bifidobacterium bifidum, Bifidobacterium catenulatum, Bifidobacterium adolescentis, Bifidobacterium thermophilum, Bifidobacterium gallicum, Bifidobacterium animalis, Bifidobacterium angulatum, Bifidobacterium pseudocatenulatum, Bifidobacterium thermacidophilum* and *Bifidobacterium longum*.

The present invention also provides a nutritional composition comprising between 5 and 25 en % protein; between 25 and 60 en % fat; between 30 and 70 en % carbohydrate; at least two different species of *Bifidobacteria* and at least one species of Lactobacillus.

The present invention also provides a container with a liquid volume between 0.5 and 50 ml containing a composition to be administered to an infant comprising at least two different microorganisms; or at least one microorganism and at least one indigestible oligosaccharide; or at least two different *Bifidobacteria* species, subspecies or strains.

In a further aspect the present invention provides a method for stimulating the development of a healthy intestinal flora in an infant comprising the step of: A) admixing I) a nutritionally or pharmaceutically acceptable liquid; and II) a dry composition, wherein the dry composition II comprises at least two different microorganisms; or at least one microorganism and at least one indigestible oligosaccharide; or at least two different *Bifidobacteria* species, subspecies or strains; and B) administering the composition obtained in step a) to an infant born via caesarean section.

The composition used in the present invention are preferably nutritional and/or pharmaceutical compositions and suitable for administration to infants.

Caesarian Section

The present invention relates to the enteral administration of a composition containing a microorganism to infants delivered via caesarean section. A caesarean section (c-section) is a surgical procedure where an infant is delivered through an incision made in the mother's abdominal wall, and then through the wall of the uterus. A caesarean section is usually performed when it is safer for the mother or the infant than a vaginal delivery. Other times, a woman may choose to have a caesarean section rather than deliver her infant vaginally.

Diversity

The present composition contains at least two different microorganisms; or at least one microorganism organism and at least one indigestible oligosaccharide; or at least two different *Bifidobacteria* species, subspecies or strains. The microorganisms are preferably bacteria and/or yeasts. Preferably the microorganisms used in the present invention are probiotic, i.e. when applied to man or animal, it beneficially affects the host by improving the properties of the indigenous microflora. The above-mentioned combinations commonly aim to increase the diversity and/or the quantity of microorganisms in the intestine of the cesarean section delivered infant. This beneficially affects the infant, proving numerous health benefits.

The term "different microorganisms" as used for the present invention refers to microorganism belonging to a different genus and/or species. Preferably the different microorganisms are different bacteria. Preferably, the different microorganisms are different species. For example and preferably, the present composition comprises or consists of *Bifidobacterium breve* (*B. breve*) and *Bifidobacterium catenulatum* (*B. catenulatum*). *B. breve* and *B. catenulatum* are herein considered as two different bacterial species. Bacterial species are not considered different if these are different subspecies. For example, *Lactobacillus delbrueckii* subspecies *delbrueckii* and *Lactobacillus delbrueckii* subspecies *bulgaricus* are not considered two different species. The present composition contains at least two different microorganisms, preferably at least two different bacterial species. Preferably the present composition contains at least three different species, more preferably at least four different species. Preferably the microorganism or bacterial species used are probiotic.

In one embodiment the present composition contains at least two different *Bifidobacteria* species, subspecies or strains. The present composition preferably comprises at least one, more preferably at least two, even more preferably at least three, most preferably at least four different *Bifidobacterium* strains. The present composition preferably comprises at least one, more preferably at least two, even more preferably at least three, most preferably at least four different *Bifidobacteria* subspecies. For example *Bifidobacterium animalis* subspecies *animalis* and *Bifidobactrium animalis* subspecies *lactis* are different subspecies. *B. breve* M16V en *B. breve* R0070 are different strains.

Microorganisms

Preferably the present composition contains at least one microorganisms selected from the group consisting of lactic acid bacteria, bacilli and yeasts, preferably at least one lactic acid bacteria selected from the group consisting of *Carnobacterium, Enterococcus, Lactobacillus, Lactococcus, Leuconostoc, Oenococcus, Pediococcus, Streptococcus, Tetragenococcus, Vagococcus* and *Weissella* and *Bifidobacteria*. The present composition preferably contains at least two, more preferably at least three, most preferably at least four different microorganisms.

Preferably the present composition contains at least one species selected from the genus *Bifidobacteria*, more preferably at least two, even more preferably at least three, more preferably at least four, most preferably at least five species from the genus of *Bifidobacteria*. *Bifidobacteria* are Gram-positive, anaerobic, rod-shaped bacteria. The present *Bifidobacterium* species preferably have at least 95% identity of the 16 S rRNA sequence when compared to the type strain of the respective *Bifidobacterium* species, more preferably at least 97% identity as defined in handbooks on this subject for instance Sambrook, J., Fritsch, E. F., and Maniatis, T. (1989), Molecular Cloning, A Laboratory Manual, 2nd ed., Cold Spring Harbor (N.Y.) Laboratory Press. The *Bifodobacteria* preferably used are also described by Scardovi, V. Genus *Bifidobacterium*. p. 1418-p. 1434. In: Bergey's manual of systematic Bacteriology. Vol. 2. Sneath, P. H. A., N. S. Mair, M. E. Sharpe and J. G. Holt (ed.). Baltimore: Williams & Wilkins. 1986. 635 p.

The present composition preferably comprises at least one, more preferably at least two, even more preferably at least three, most preferably at least four *Bifidobacterium* species preferably selected from the group consisting of *Bifidobacterium breve, Bifidobacterium infantis, Bifidobacterium bifidum, Bifidobacterium catenulatum, Bifidobacterium adolescentis, Bifidobacterium thermophilum, Bifidobacterium gallicum, Bifidobacterium animalis, Bifidobacterium angulatum, Bifidobacterium pseudocatenulatum, Bifidobacterium thermacidophilum* and *Bifidobacterium longum*. More preferably the present composition preferably comprises at least one, more preferably at least two, even more preferably at least three, most preferably at least four *Bifidobacterium* species preferably selected from the group consisting of *Bifidobacterium breve, Bifidobacterium infantis, Bifidobacterium bifidum, Bifidobacterium catenulatum, Bifidobacterium adolescentis* and *Bifidobacterium longum*. Most preferably the present composition contains *Bifidobacterium breve* and/or *Bifidobacterium catenulatum*.

In a further preferred embodiment, the present composition comprises at least one, more preferably at least two, even more preferably at least three, most preferably at least four *Bifidobacterium* subspecies. In still a further preferred embodiment, the present composition comprises at least one, more preferably at least two, even more preferably at least three, most preferably at least four *Bifidobacterium* strains.

In a further preferred embodiment, the present composition contains a lactic acid bacteria, preferably at least a bacteria selected from the group consisting of *Lactobacilli, Lactococci* and *Streptococci*. More preferably the present composition contains at least one bacteria selected from the group consisting of *Lactobacillus plantarum, Lactobacillus reuteri, Lactobacillus johnsonii, Lactobacillus casei, Lactobacillus rhamnosus, Lactobacillus acidophilus, Lactobacillus fermentum, Lactobacillus lactis, Streptococcus thermophilus* and *Lactobacillus paracasei*. The further increased biodiversity will have a stimulatory effect on health of the newborn.

The present composition preferably contains between $10^1$ and $10^{13}$ colony forming units (cfu) microorganisms per gram dry weight of the present composition, preferably between $10^2$ and $10^{12}$, more preferably between $10^3$ and $10^{10}$. Preferably, the present composition contains between $10^1$ and $10^{13}$ colony forming units (cfu) *Bifidobacteria* per g dry weight of the present composition, more preferably between $10^2$ and $10^{12}$, most preferably between $10^3$ and $10^{12}$.

The present method preferably comprises the administration of a serving containing between $10^1$ and $10^{13}$ cfu microorganisms more preferably between $10^2$ and $10^{11}$, most preferably between $10^3$ and $10^{10}$. The present method preferably comprises the administration of a serving containing between $10^1$ and $10^{13}$ cfu *Bifidobacteria*, more preferably between $10^2$ and $10^{12}$, most preferably between $10^3$ and $10^{11}$.

Oligosaccharides

The term "indigestible oligosaccharides" as used in the present invention refers to oligosaccharides/carbohydrates which are not or only partially digested in the intestine by the action of acids or digestive enzymes present in the human upper digestive tract (small intestine and stomach) but which are fermented by the human intestinal flora. Preferably the present indigestible oligosaccharide has a degree of polymerisation (DP) of 2 to 100, preferably a DP 2 to 50.

Preferably the present indigestible oligosaccharide is a prebiotic fiber. The term "prebiotic fiber" refers to non-digestible fibers that beneficially affects the host by selectively stimulating the growth and/or activity of one or a limited number of bacterial species in the colon.

Preferably the present indigestible oligosaccharide is soluble. The term "soluble" as used herein, when having reference to a polysaccharide, fibre or oligosaccharide, means that the substance is at least 50% soluble according to the method described by L. Prosky et al., J. Assoc. Off. Anal. Chem. 71, 1017-1023 (1988).

Preferably the present composition contains at least one oligosaccharide selected from the group consisting of galactooligosaccharides, indigestible dextrins, xylooligosaccharides, arabinooligosaccharides, glucooligosaccharides, mannooligo-saccharides, isomalto-oligosaccharide and fructopolysaccharide.

The term "fructopolysaccharide" as used herein refers to a polysaccharide carbohydrate comprising a chain of at least 3 β-linked fructose units, with a DP between 3 and 300, preferably between 20 and 150. Preferably inulin is used. Inulin is available under the tradename "Raftilin HP®", (Orafti). The average DP of the fructopolysaccharide is preferably at least 15, more preferably at least 20 or more, up to 300. In inulin the fructose units are linked with a β(2→1) linkage.

Indigestible polydextrins refer to digestion-resistant (malto)dextrins or digestion-resistant polydextrose which have a DP of 10 to 50, preferably between 10 and 20. The indigestible polydextrins comprise α(1→4), α(1→6) glucosidic bonds and 1→2 and 1→3 linkages Indigestible polydextrins are for example available under the tradename "Fibersol 2®" from Matsutami Inductries or Litesse® from Danisco.

The present inventors found that galactooligosaccharides can be advantageously used in the present composition, because these oligosaccharides where particularly effective in stimulating the growth of *Bifidobacteria*. Hence, in a preferred embodiment the present composition contains galactooligosaccharides. The term "galactooligosaccharide" as used herein refers to an indigestible saccharide, wherein at least 30% of the saccharide units are galactose units, preferably at least 50%, more preferably at least 60%. Preferably the saccharides of the galactooligosaccharide are (β-linked, as is the case in human milk.

Preferably the present composition contains a galactooligosaccharide selected from the group consisting of transgalactooligosaccharides, lacto-N-tetraose (LNT) and lacto-N-neotetraose (neo-LNT). In a particularly preferred embodiment the present method comprises the administration of transgalactooligosaccharide ([galactose])$_n$-glucose; wherein n is an integer between 1 and 60, i.e. 2, 3, 4, 5, 6, . . . , 59, 60; preferably n is selected from 2, 3, 4, 5, 6, 7, 8, 9, or 10). Transgalactooligosaccharides (TOS) are for example sold under the trademark Vivinal™ (Borculo Domo Ingredients, Netherlands). Preferably the saccharides of the transgalactooligosaccharides are β-linked.

The present composition preferably contains 0.5 to 75 grams of the indigestible soluble oligosaccharides per 100 gram dry weight, preferably between 0.5 and 50 grams. The present composition preferably comprises 0.1 to 95 grams of the galactooligosaccharides per 100 gram dry weight, preferably between 0.1 and 50 grams.

The present method preferably comprises the administration of a serving containing between 0.05 and 25 grams indigestible oligosaccharide, preferably between 0.1 and 5 grams. The present method preferably comprises the administration of a serving containing between 0.05 and 25 grams galactooligosaccharides, preferably between 0.1 and 5 gram galactooligosaccharides.

The present inventors have also found that a mixture of a long chain indigestible oligosaccharides and short chain indigestible oligosaccharides synergistically stimulate the growth of a healthy intestinal flora, particularly *Bifidobacteria*. Hence the present composition preferably contains at least two oligosaccharides with different average degrees of polymerization (DP). Preferably the weight ratios:
a. (indigestible oligosaccharides with DP 2 to 5):(indigestible oligosaccharides with DP 6, 7, 8, and/or 9)>1; and
b. (indigestible oligosaccharides with DP 10 to 60):(indigestible oligosaccharides with DP 6, 7, 8, and/or 9)>1

Preferably both weight ratios are above 2, even more preferably above 5.

For further improvement, the oligosaccharide preferably has a relatively high content of short chain oligosaccharides, as these strongly stimulate the growth of *Bifodobacteria*. Hence, preferably at least 10 wt. % of the oligosaccharides in the present composition has a DP of 2 to 5 (i.e. 2, 3, 4, and/or 5) and at least 5 wt. % has a DP of 10 to 60. Preferably at least 50 wt. %, more preferably at least 75 wt. % of the oligosaccharides have a DP of 2 to 9 (i.e. 2, 3, 4, 5, 6, 7, 8, and/or 9).

To improve the biodiversity and stimulate the growth of multiple intestinal organisms, the present composition preferably comprises two oligosaccharides with a different structure. The present composition comprises at least two different oligosaccharides, wherein the oligosaccharides have a homology in saccharide units below about 90%, preferably below 50%, even more preferably below 25%, even more preferably below 5%. The term "homology" as used in the present invention is the cumulative of the percentage of same saccharide unit in the different oligosaccharides. For example, oligosaccharide 1 (OL1) has the structure fruc-fruct-glu-gal, and thus comprises 50% fruc, 25% gal and 25% glu. Oligosaccharide 2 (OL2) has the structure fruc-fruc-glu, and thus comprises 66% fruc, 33% glu. The different oligosaccharides thus have a homology of 75% (50% fruc+25% glu).

Preferably the present composition contains galactooligosaccharides and fructopolysaccharides.

Application

The present composition is preferably enterally administered, more preferably orally. The present composition is therefore preferably a liquid. The term "enteral" here used also encompasses a rectal or anal administration.

When infants receive infant milk formula, the present composition with microorganisms and optionally including at least one indigestible oligosaccharide, is preferably included in the nutritional formula. The probiotic and/or prebiotic may be separately added to the infant formula. When newborns receive nutrition via a tube, the microorganisms can be suitably included in the nutrition administered via tube. Stimulating diversity is of great importance, thus the present invention also provides a nutritional composition comprising between 5 and 25 en % protein; between 25 and 60 en % fat; between 30 and 70 en % carbohydrate; at least two different species of *Bifidobacteria* and at least one species of *Lactobacillus*.

When infants receive human breast milk, the present composition can be suitably admixed with human breast milk. The present invention consequently also provides a method for the manufacture of infant nutrition suitable for infant born via cesarean section comprising admixing: A) human breast milk; and B) a composition comprising: (i) at least two different microorganisms; or (ii) at least one microorganism and at least one indigestible oligosaccharide; or (iii) at least two different *Bifidobacteria* species, subspecies or strains. The preferred characteristics of composition B) are as provided hereinabove.

In a further preferred embodiment the present composition is administered to the infant in a very small volume, e.g. by "inoculating" the infant. Preferably, the present composition is administered to the infant with a syringe, pipette or tube, preferably directly after birth. In a further preferred embodiment, the present composition is rectally or anally administered to the infant delivered via caesarean section, preferably in the form of a suppository, pill or tablet. Hence, the present invention also provides a suppository, pill or table suitable for rectal administration to a infant with the age below one year, wherein said suppository, pill or tablet contains microorganisms and/or indigestible oligosaccharides, preferably the present composition as described hereinabove.

In a further preferred embodiment the present invention provides a method stimulating the intestinal flora of an infant comprising rectally administering to an infant with the age below 3 year a composition comprising microorganism and/or indigestible oligosaccharide. Preferably the infant has an age below 1 year, more preferably below 2 weeks. Preferably the infant is delivered via caesarean section. Preferably this composition for rectal administration contains the above-described composition.

This procedure has the advantage that it does not interfere with the normal breast-feeding practice and has high resemblance with vaginal inoculation, which occurs during birth. The present invention also provides a method for stimulating the health of an infant delivered via caesarean section, comprising administering to the infant and within 100 hours after birth, preferably within 72 hours after birth, most preferably within 48 hours after birth, a composition containing microorganisms and/or indigestible oligosaccharides.

The composition is preferably suitable for administration directly after birth. Hence, in a further preferred embodiment, the present invention provides a container comprising a liquid composition with a volume between 0.5 and 50 ml, which contains the present composition. The liquid with the present microorganism, optionally combined with indigestible oligosaccharides, can be suitably used in the present method. Preferably the liquid has a volume between 0.5 and 25 ml. This volume is preferably small, because it otherwise could interfere with the appetite and drinking behaviors of the infant.

Similarly and encompassed by this invention is a container with a reconstitutable dry composition containing the present composition, wherein the container has a volume of between 0.5 and 50 ml. This container is preferably accompanied with instruction to reconstitute the powder in a small volume of liquid, e.g. water.

The present invention thus also provides a method for stimulating the development of a healthy intestinal flora in an infant comprising step A: admixing I) an in particular nutritionally or pharmaceutically acceptable liquid; and II) a dry composition, wherein the dry composition II comprises at least two different microorganisms; or at least one microorganism and at least one indigestible oligosaccharide; or at least two different *Bifidobacteria* species, subspecies or strains; and step B) administering the composition obtained in step a) to an infant born via caesarean section.

The present composition is preferably administered to the infant in the first year of life, preferably within two weeks after birth, even more preferably within one week after birth, most preferably within 48 hours after birth.

EXAMPLES

Example 1

Molecular Characterization of Intestinal Microbiota in Infants Born by Vaginal Delivery vs. Caesarean Delivery In the present study the influence of mode of delivery (caesarean delivery versus vaginal delivery) on the intestinal microbial composition at the third day of life by using PCR-Denaturing Gradient Gel Electrophoresis (DGGE) and PCR-Temperature Gradient Gel Electrophoresis (TGGE). Both DGGE and TGGE analyses have been utilized, together with the specific amplifications for ten *Bifidobacterium* species.

After written informed consent had been obtained from the parents twenty-three newborns after caesarean delivery and vaginal delivery have been enrolled in the study. The faecal samples were obtained on the third day of life.

The microbial DNA was extracted and analysed according to Favier et al, Environ Microbiol 2002; 68:219-226 and Satokari et al, Appl Environ Microbiol 2001; 67:504-513; Satorkari et al System Appl Microbiol 2003; 26:572-584.

The results of the *Bifidobacteria* detected in faecal samples of newborns after caesarean delivery obtained at the 3rd day of life are given in Table 1. Table 2 gives the *Bifidobateria* detected in faecal samples of newborn after vaginal delivery obtained at the 3rd day of life.

It can be seen that the microbial flora of a infant born via caesarean section shows strong differences with a infant born via the vaginal route. Recognition of these differences on species level enabled the present inventors to design the present compositions and methods.

These results are indicative for the advantageous use of the composition and method according to the present invention, e.g. a method for feeding babies born via caesarean section, stimulating a healthy intestinal flora and consequently preventing infection and stimulating a healthy immune system.

TABLE 1

| | | | | | | | | | | |
|---|---|---|---|---|---|---|---|---|---|---|
| | | | | | Caesarean | | | | | |
| NEWBORN | B. breve | B. infantis | B. dentium | B. angulatum | B. bifidum | B. lactis | B. catenulatum group | B. adolescentis | B. longum | B. gallicum |
| 1 | − | − | − | − | − | − | − | − | − | − |
| 2 | − | − | − | − | − | − | − | − | ++ | − |
| 3 | − | − | − | − | − | − | − | − | − | − |
| 4 | − | − | − | − | − | − | − | − | − | − |
| 5 | − | − | − | − | − | − | − | − | − | − |
| 6 | − | − | − | − | − | − | − | − | − | − |
| 7 | − | − | − | − | − | − | − | − | − | − |
| 9 | − | − | − | − | − | − | − | − | − | − |
| 10 | − | − | − | − | − | − | − | − | − | ++ |
| 11 | − | − | − | − | − | − | − | − | − | − |
| 12 | − | − | − | − | − | − | − | − | − | − |
| 13 | − | − | − | − | − | − | − | − | − | − |
| 16 | − | − | − | − | − | − | − | − | − | − |
| 17 | − | − | − | − | − | − | − | − | − | − |
| 18 | − | − | − | − | − | − | − | − | − | − |
| 19 | − | − | − | − | − | − | − | − | − | − |
| 20 | − | − | − | − | − | − | − | − | − | − |
| 21 | − | − | − | − | − | − | − | − | − | − |
| 22 | − | − | − | − | − | − | − | − | − | − |
| 23 | − | − | − | − | − | − | − | − | − | − |

(−) = no amplification
(+/−) = weak amplification
(+) = positive amplification
(++) = strong amplification

TABLE 2

| NEWBORN | B. breve | B. infantis | B. dentium | B. angulatum | B. bifidum | B. lactis | B. catenulatum group | B. adolescentis | B. longum | B. gallicum |
|---|---|---|---|---|---|---|---|---|---|---|
| 1a | − | + | − | − | − | − | − | − | ++ | − |
| 2a | +/− | − | − | − | ++ | − | ++ | − | ++ | − |
| 3a | − | − | − | − | − | − | + | − | − | − |
| 4a | +/− | − | − | − | − | − | ++ | + | + | − |
| 5a | +/− | − | − | − | ++ | − | ++ | − | ++ | ++ |
| 6a | − | − | − | − | +/− | − | ++ | − | ++ | − |
| 7a | − | − | − | − | +/− | − | ++ | ++ | − | − |
| 8a | ++ | ++ | − | − | − | − | + | ++ | − | − |
| 9a | − | − | − | − | − | − | + | ++ | + | − |
| 10a | ++ | − | − | − | − | − | + | + | − | − |
| 11a | ++ | − | − | − | ++ | − | ++ | − | ++ | − |
| 12a | + | + | − | − | + | − | + | − | ++ | − |
| 13a | +/− | − | − | − | − | − | + | − | + | − |
| 16a | − | − | − | − | − | − | ++ | − | + | − |
| 17a | +/− | − | − | − | + | − | + | − | + | − |
| 18a | +/− | − | − | − | + | − | + | − | + | − |
| 19a | + | − | − | − | − | − | + | − | + | − |
| 20a | − | − | − | − | − | − | + | − | + | − |
| 21a | − | − | − | − | − | − | + | ++ | + | − |
| 22a | − | + | − | − | − | − | ++ | − | + | − |
| 23a | + | − | − | − | ++ | − | ++ | − | + | − |

(−) = no amplification
(+/−) = weak amplification
(+) = positive amplification
(++) = strong amplification Example 2

In Vitro Fermentation of Galacto-Oligosaccharide by Infant's Faeces

Aim: The capacity of galactooligosaccharides (GOS) and a combination of GOS and inulin to favor the activity of lactic acid bacteria was evaluated using an in vitro semi dynamic batch fermentation system using infants faeces. The amount of lactate was determined, since this is the fermentation product of lactic acid bacteria including *Bifidobacteria*.

Method: Fresh faeces was obtained from healthy bottle-fed babies. Fresh faecal material from babies ranging 1 to 4 months of age was pooled and put into a preservative medium (buffered peptone 20.0 g/l, L-Cysteine-HCl 0.5 g/l, Sodium thioglycollate 0.5 g/l, resazurine tablet 1/1, pH 6.7) within 1 h and stored at 4° C. for at most 2 h before the fermentation experiment was started.

The preserved solution of faeces was centrifuged at 13,000 rpm for 15 min. The supernatant was removed and the faces was mixed with McBain & MacFarlane medium (Buffered peptone water 3.0 g/l, yeast extract 2.5 g/l, mucin (brush borders) 0.8 g/l, Tryptone 3.0 g/l, L-Cysteine-HCl 0.4 g/l, bile salts 0.05 g/l, $K_2HPO_4 \cdot 3H_2O$ 2.6 g/l, $NaHCO_3$ 0.2 g/l, NaCl 4.5 g/l, $MgSO_4 \cdot 7H_2O$ 0.5 g/l, $CaCl_2$ 0.228 g/l, $FeSO_4$ 0.005 g/l), which is representative for the intestinal environment, in a weight ratio of 1:5.

At t=0.15 ml of the faecal suspension was combined with 500 mg prebiotic in a bottle and mixed thoroughly. As a control no prebiotic was added. The prebiotics added were as followed:

| Media: | 1 | 2 | 3 |
|---|---|---|---|
| GOS: | 0 | 500 | 450 |
| Insulin: | 0 | 0 | 50 |

As a source of GOS, Vivinal GOS (Borculo Domo) was used. As a source of inulin RaftilinHP (Orafti) was used.

15 ml was transferred into a dialysis tube in a 250 ml bottle filled with 250 ml of buffered medium ($K_2HPO_4 \cdot 3H_2O$ 2.6 g/l, $NaHCO_3$ 0.2 g/l, NaCl 4.5 g/l, $MgSO_4 \cdot 7H_2O$ 0.5 g/l, $CaCl_2$ 0.228 g/l, $FeSO_4 \cdot 7H2O$ 0.005 g/l pH 6.3(?)). The bottle was closed and incubated at 37° C. Samples of 1 ml were taken from the dialysis tube and from the dialysis buffer with a hypodermic syringe after 3 h and stored at −18° C. Experiments were performed in duplo. Lactate was determined enzymatically, using a L-lactate acid detection kit with D- and L-lactate-dehydrogenase (Boehringer Mannheim, Mannheim, Germany).

Results and Conclusions: The results are expressed as amounts of lactate formed per g of prebiotic added. The results show that the amount of lactate is increased when an infant's microflora ferments GOS or a mixture of GOS and inulin. When no prebiotic was added, lactate production is not observed. With GOS alone 0.1801 mmol/g prebiotic lactate is produced. When a combination of GOS and inulin is added the lactate produced is 0.2119 mmol per g prebiotic.

The results indicate that the oligosaccharides stimulate the growth and/or activity of lactic acid bacteria in infants, including *Bifidobacteria*. These results are indicative for the advantageous use of the indigestible oligosaccharides, particularly galactooligosaccharides, in the present composition and method according to the present invention, i.e. in a method for feeding babies born via caesarean section.

Example 3

Method for Feeding Babies Born via Caesarean Section

Within two days after the infant is born via caesarean section, a nutritional composition is administered which contains per 100 ml ready to feed formula: 1.6 gram protein, 3.6 gram fat, 6.4 gram digestible carbohydrates (mainly lactose), 0.8 gram non-digestible carbohydrates of which 0.60 gram transgalactooligosaccharides, 0.07 gram inulin, 1×10$^9$ cfu *Bifidobacterium breve*, 1×10$^9$ cfu *Bifidobacterium catenulatum*, 1×10$^9$ cfu *Bifidobacterium longum* and 1×10$^9$ cfu *Lactobacillus paracasei*.

Example 4

Packaged Composition

Packaged composition wherein the package indicates that the product is particular suitable for oral feeding infants born via Caesarean section, said composition comprising *Bifidobacterium breve, Bifidobacterium infantis, Bifidobacterium bifidum, Bifidobacterium catenulatum, Bifidobacterium adolescentis, Bifidobacterium longum*, galactooligosaccharides and inulin.

Example 5

Packaged Composition

Composition as in Example 4, wherein the composition has a volume of 10 ml and is packed in a syringe.

Example 6

Rectal Administration

P11 suitable for rectal administration to an infant within two weeks after birth, comprising galactooligosaccharides and *Bifidobacterium breve, Bifidobacterium infantis, Bifidobacterium bifidum*.

The invention claimed is:

1. A method for feeding an infant delivered via caesarean section, comprising:
   (i) identifying an infant delivered via caesarean section; and
   (ii) enterally administering to the infant starting within 100 hours after birth a composition comprising:
      (a) between 10$^3$ and 10$^{13}$ colony forming units (cfu) *Bifidobacterium* consisting of *Bifidobacterium breve*; and
      (b) between 0.1 and 5 grams indigestible galacto-oligosaccharides per serving.

2. The method of claim 1, wherein the composition further comprises an indigestible oligosaccharide selected from the group consisting of indigestible dextrins, xylooligosaccharides, arabinooligosaccharides, glucooligosaccharides, mannooligo-saccharides, isomalto-oligosaccharide and fructo-polysaccharides.

3. The method of claim 1, wherein the composition comprises between 5 and 25 energy % protein, between 25 and 60 energy % fat and between 30 and 70 energy % carbohydrate.

4. The method of claim 1, wherein the composition is administered to an infant receiving human breast milk.

5. The method of claim 1, wherein the composition is admixed with a nutritionally or pharmaceutically acceptable liquid prior to administering the composition to the infant.

6. The method of claim 1, wherein the administration stimulates the intestinal flora of the infant.

7. The method of claim 1, wherein the composition is administered to the infant starting within 48 hours after birth.

* * * * *